United States Patent [19]
Podszun et al.

[11] Patent Number: 5,849,270
[45] Date of Patent: Dec. 15, 1998

[54] DENTAL ADHESIVES

[75] Inventors: Wolfgang Podszun, Köln; Werner Finger, Neuss, both of Germany

[73] Assignee: Heraeus Kulzer GmbH, Hanau, Germany

[21] Appl. No.: 787,127

[22] Filed: Jan. 22, 1997

[30] Foreign Application Priority Data

Feb. 1, 1996 [DE] Germany ............. 196 03 577.5

[51] Int. Cl.⁶ .................................................. A61K 7/24
[52] U.S. Cl. ..................... 424/55; 526/304; 523/111; 523/118; 523/120
[58] Field of Search ................ 424/55; 526/304; 523/111, 118, 120

[56] References Cited

U.S. PATENT DOCUMENTS

| | | | |
|---|---|---|---|
| 4,323,696 | 4/1982 | Schmitz-Josten et al. . | |
| 4,437,836 | 3/1984 | Schmitz-Josten et al. . | |
| 4,879,402 | 11/1989 | Reiners, II et al. . | |
| 4,952,614 | 8/1990 | Reiners, I et al. . | |
| 4,968,725 | 11/1990 | Mukai et al. ................. | 522/90 |
| 5,122,061 | 6/1992 | Wakumoto et al. ........... | 433/228 |
| 5,264,485 | 11/1993 | Muller et al. ................. | 524/724 |
| 5,264,513 | 11/1993 | Ikemura et al. ............... | 526/318 |
| 5,354,827 | 10/1994 | Müller et al. . | |
| 5,444,104 | 8/1995 | Waknine ....................... | 552/24 |

FOREIGN PATENT DOCUMENTS

| | | |
|---|---|---|
| 0 023 686 B1 | 2/1981 | European Pat. Off. . |
| 0 254 950 B1 | 2/1988 | European Pat. Off. . |
| 0 361 033 B1 | 4/1990 | European Pat. Off. . |
| 31 35 113 A1 | 3/1983 | Germany . |
| 37 03 080 A1 | 1/1988 | Germany . |
| 37 03 120 A1 | 1/1988 | Germany . |
| 37 03 130 A1 | 1/1988 | Germany . |
| 38 28 170 A1 | 2/1990 | Germany . |
| 41 05 550 A1 | 8/1992 | Germany . |

*Primary Examiner*—James H. Reamer
*Attorney, Agent, or Firm*—Frishauf, Holtz, Goodman, Langer & Chick, P.C.

[57] ABSTRACT

The adhesion of resin material to the solid substance of the tooth and to metals and metal alloys, for example, dental alloys, can be improved with a photo-polymerizable formulation containing hydroxyalkyl(meth)acrylates, urethanedi (meth)acrylates and, if applicable, esters of aromatic polycarboxylic acids possessing methacryloyloxy groups.

12 Claims, No Drawings

DENTAL ADHESIVES

FIELD OF THE INVENTION

The invention relates to a formulation for use as an adhesive component particularly in the treatment of the hard substance of the tooth and of dental alloys.

Tooth hard substance is built up from tooth enamel and dentine, which differ greatly in their composition. Tooth enamel is built up largely on a mineral basis, in particular from hydroxyapatite. Dentine, in contrast, consists to a considerable proportion, of organic units, such as collagen and other proteins, and contains more water. A specific serious problem in the field of conservative dentistry is to form a durable gap free bond of resin based curable dental filling materials normally used in dentistry, with the hard substance of the tooth (dentin and tooth enamel).

DESCRIPTION OF RELATED ART

In order to improve bonding with the hard substance of the tooth, so-called dental adhesives or bonding agents are used. In this context, dental adhesives are preferred which not only produce good adhesive values with respect to the dentin but also with respect to the enamel. Generally, it is expected that, to obtain an effective formulation, a plurality of components must be used. Thus, for example, in DE-A-38 28 170 and EP-B-0361033, a coating substance for collagen-containing materials is described, which consists of a) aldehyde
b) a water-soluble monomer with active hydrogen,
c) a water-insoluble monomer with two or more polymerizable double bonds,
d) a photo-initiator,
e) water,
f) a solubility agent and/or dispersant and
g) known additives.

With this coating agent it is possible to achieve bonding strengths of 11.8–19 N/mm$^2$ to dentin and 12.6–17 N/mm$^2$ to enamel.

In U.S. Pat. No. 5,354,827 (and DE-A-41 05 550) a dental adhesive formulation consisting of a) (meth)acrylic acid esters containing formamide groups,
b) (meth)acrylic esters which can form cross-linkings,
c) solvents,
d) optionally other additives,
e) acids and,
f) optionally, a dispersant is described. With this formulation it is possible to achieve bonding strengths of 7.2–9.9 N/mm$^2$ to dentin and 9.6–14.4 N/mm$^2$ to enamel.

These are the type of dental adhesives or bonding agents over which the present invention provides an improved formulation.

SUMMARY OF THE INVENTION

A formulation has now been discovered which contains only a few components, is easy to use and enables very high adhesive values with respect to enamel, dentin, ceramics, metals and metal alloys. The formulation according to the invention contains:

a) 10–40% by weight of hydroxyalkyl(meth)acrylate,
b) 10–40% by weight of urethanedi(meth)acrylate,
c) 30–70% by weight of a volatile solvent miscible with water,
d) 0.01–2.5% by weight of a photo-initiator and
e) 0–40% by weight of generally known additives.

DESCRIPTION OF THE PREFERRED EMBODIMENTS

The invention is an adhesive especially for use in conservative dentistry. It has the following composition:

a) 10–40% by weight of hydroxyalkyl(meth)acrylate,
b) 10–40% by weight of urethanedi(meth)acrylate,
c) 30–70% by weight of a volatile solvent miscible with water,
d) 0.01–2.5% by weight of a photo-initiator and
e) 0–40% by weight of generally known additives.

Hydroxyalkyl(meth)acrylates in the context of the present invention are esters of polyols possessing hydroxyl groups, preferably of glycols, with acrylic acid or methacrylic acid. As examples, the following compounds are listed: 2-hydroxyethylacrylate, 2-hydroxyethylmethacrylate, 2-hydroxypropylacrylate, 2-hydroxypropylmethacrylate and 2,3-dihydroxypropylmethacrylate (glycerol monomethacrylate). 2-hydroxyethylmethacrylate and 2,3-dihydroxypropylmethacrylate (glycerol monomethacrylate) are preferred.

The urethanedi(meth)acrylates according to the invention are reaction products of diisocyanates with hydroxyalkyl-(meth) acrylates. The urethanedi(meth)acrylates can derive from aliphatic, branched aliphatic, cycloaliphatic or aromatic diisocyanates. Reaction products of aliphatic, branched aliphatic and cycloaliphatic diisocyanates are preferred. The following urethanediacrylates (UDA) and urethanedimethacrylates (UDM) are examples of useful urethanedi(meth)acrylates for the present invention formulation:

UDM 1
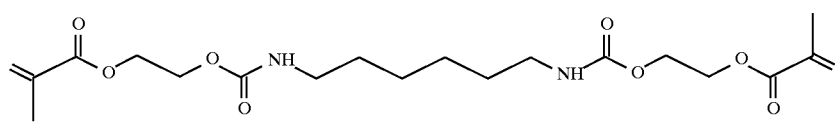

UDM 2
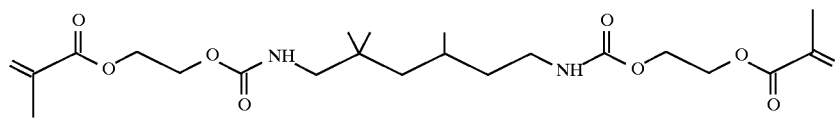

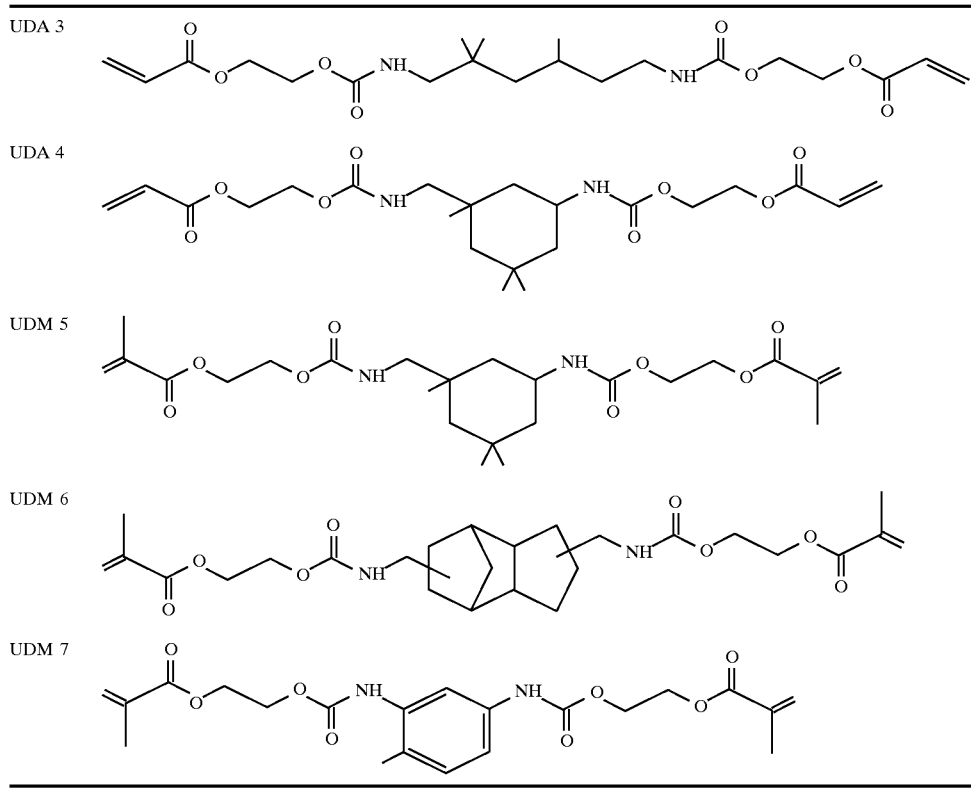

Volatile solvents miscible with water are primarily those with a vapor pressure of a minimum of 100 torr at ambient temperature. Aliphatic alcohols with one to four carbon atoms, acetone, 1,4-dioxane and tetrahydrofurane are preferred. Acetone and ethyl alcohol are particularly preferred.

In the context of the present invention, photo-initiators form free radicals which initiate radical polymerization when irradiated with light, for example, UV light, visible light or laser light.

These photo-polymerization initiators are generally known from the literature e.g. U.S. Pat. No. 5,354,827 and U.S. Pat. No. 4,437,836. Preferably, they are mono- or dicarbonyl compounds such as benzophenone; benzoin and its derivatives, in particular benzoin methyl ether; benzil and benzil derivatives; other dicarbonyl compounds, such as diacetyl, 2,3-pentanedione and α-diketo derivatives of norbornane and substituted norbornanes; metal carbonyls, such as pentacarbonyl manganese; or quinones such as 9,10-phenanthrene quinone and naphthoquinone. Camphor quinone is especially preferred.

The formulation according to the invention generally contains 0.01 to 2.5% by weight, preferably 0.1 to 0.5% by weight, of a photo-initiator, with respect to the total weight of the formulation.

It can be advantageous to add co-activators (or accelerators) to the formulation according to the invention, which accelerate the photo-polymerization reaction. These are also well-known in the art (e.g. UK 1,408,265, U.S. Pat. No. 5,354,827 and U.S. Pat. No. 4,437,836). Known co-activators are, for example, amines, such as p-toluidine, dimethyl-p-toluidine; trialkylamines, such as trihexylamine; polyamines, such as N,N,N',N'-tetraalkylalkylen-diamines; barbituric acid and dialkyl barbituric acids. Dimethylaminobenzenesulphonamides as described in DE-A-31 35 113 or U.S. Pat. No. 4,437,836 are particularly preferred.

Co-activators are generally used in a quantity of 0.02 to 4% by weight, 0.2 to 1% by weight being preferred, with respect to the total weight of the formulation according to the invention.

In addition to hydroxy(meth)acrylate, urethanedi(meth)acrylate, solvent, photo-initiator and co-activator, the formulation according to the invention can, optionally, contain additional (meth)acrylic esters as co-monomers, in particular are esters of (meth)acrylic acid with mono- to pentahydric alcohols with 2 to 30 carbon atoms.

Also found particularly useful are tricyclodecane derivatives (as described e.g. in EP-A-0 023 686 or U.S. Pat. No. 4,323,696) and reaction products from polyols, diisocyanates and hydroxyalkylmethacrylates (as described e.g. in DE-A-37 03 120 or U.S. Pat. No. 4,952,614, DE-A-37 03 080 or EP-B-0 254 950 and DE-A-37 03 130 or U.S. Pat. No. 4,879,402).

Particularly preferred as (meth)acrylic ester is the so-called Bis-GMA with the formula

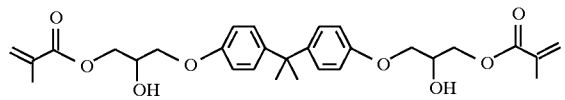

The formulation according to the invention not only enables strong bonding of synthetic material to dentin and enamel but also to ceramics, metals and metal alloys.

In a special embodiment of the invention, the formulation according to the invention contains esters of aromatic tri- or tetracarboxylic acids possessing methacryloyloxy groups for further improving the adhesion of resin material to metals, preferably with dental alloys. Instead of the tri- or tetracarboxylic acids, one can also use the corresponding derivatives in which two adjacent carboxyl groups form an anhydride group. As suitable esters of aromatic tri- or tetracarboxylic acids possessing methacryloyloxy groups the following compounds are listed as examples:

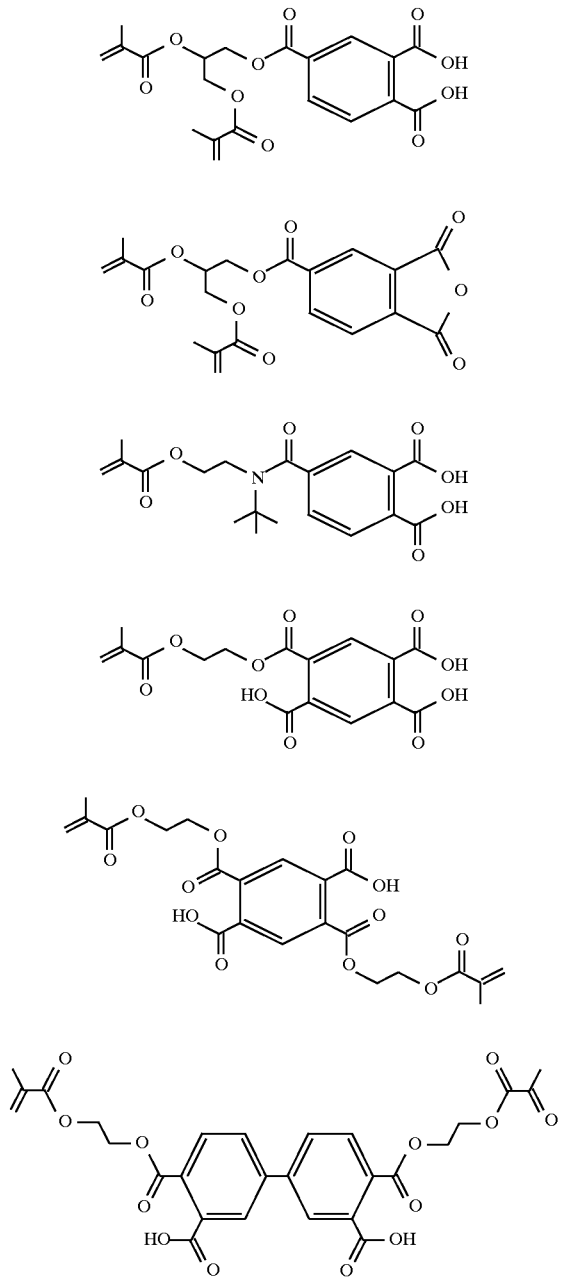

Particularly suitable are trimellitic acid derivatives which are designated as "4-MET" and "4-META" in technical literature and have the formulas, respectively:

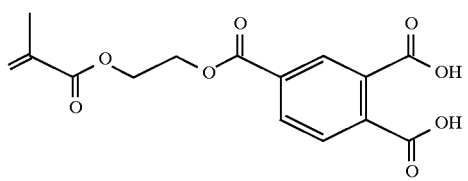

-continued

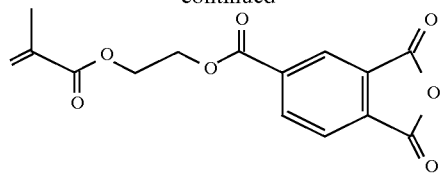

The esters of aromatic tricarboxylic acids possessing methacryloyloxy groups are used in amounts of 2 to 30% by weight, preferably 5 to 20% by weight, with respect to the total weight of the formulation.

It is possible to obtain a particularly good elasticity in a layer made of the formulation and cured by polymerization with a formulation which additionally contains polyethylene glycoldi(meth)acrylates, in particular, polyethylene glycol di(meth)acrylates with a molecular weight of 200–2000. Other additives to improve the elastic properties can consist of polyester methacrylates or polyester polyurethane (meth) acrylates or other polyether (meth)acrylates. These additives are applied in quantities of 1 to 30% by weight, preferably 5 to 20% by weight, with respect to the formulation.

It has been found that the generally very high adhesive values with respect to dentin can be further increased by adding a fine particle sized inorganic filler. Suitable fillers are, for example, quartz, cristobalite, vitreous silica, highly dispersed silica, aluminum oxide and glass-ceramics. The mean particle size of the inorganic fillers is generally in the range of 5–2000 nm, preferably in the range of 10–100 nm. Particularly suitable inorganic fillers are highly dispersed silicas, which, for example, can be produced by flame hydrolysis. Particularly effective are additives in a quantity of 5 to 20% by weight, with respect to the total weight of the formulation.

Preferably, the fillers are pretreated, for example, with silanization agents consisting of organosilane compounds (Progress in Organic Coatings 11, 297–308 (1983)). A preferred silanization agent is 3-methacryloyloxypropyl-trimethoxysilane.

The formulation according to the invention can furthermore contain generally known or standard additives such as stabilizers, inhibitors and light stabilizers.

The formulation according to the invention can be produced in a simple manner by mixing the individual components.

In a preferred embodiment of the invention, a diisocyanate and a surplus of hydroxyalkyl(meth)acrylate are mixed together in a suitable solvent such as acetone in the presence of a catalyst, the result being a mixture of hydroxyalkyl (meth)acrylate, urethanedi(meth)acrylate and solvent. As a catalyst, metallic salts of higher fatty acids, such as dibutyl tin-dilaurate, triaryl compounds, such as triphenylstibine or triphenylphosphine, or tertiary amines, such as triethylamine, can be used. By adding a photo-initiator and, optionally, additional additives to the mixture, a formulation according to the invention is obtained.

The formulation according to the invention is suitable as adhesive component for use with ceramics, metals and metal alloys, and is preferably used on the hard substance of the tooth and dental alloys.

In a special embodiment, prior to treatment with the formulation according to the invention, the hard substance of the tooth is conditioned with a conditioning fluid which has a pH value in the range of 0.1 to 3.5. This conditioning fluid generally contains acids with a $pK_a$ value less than 5 and, if applicable, an amphoteric amino compound with a $pK_a$ value in the range of 9.0 to 10.6 and a $pK_b$ value in the range of 11.5 to 12.5. The following acids, for example, can be used in the conditioning fluid: phosphoric acid, nitric acid, pyruvic acid, citric acid, oxalic acid, ethylenediamine tetraacetic acid, acetic acid, tartaric acid and malic acid. Furthermore, the conditioning fluid can contain polyethylene glycols and/or metal hydroxides. In particular, the above listed polybasic acids can also be in the form of partial metallic salts, as long as free acid functions remain. Treatment with a dilute phosphoric acid is preferred. Suitable concentrations of phosphoric acid are 10–60% by weight, preferably 20–40%. The conditioning fluid may contain thickening agents, for example, fine sized silica, to obtain a fluid with suitable consistency.

Use of the formulation according to the invention can, for example, be carried out as follows:

When performing dental restoration, after mechanically cleaning the tooth surface, one first applies the conditioning fluid to the tooth surface, allows it to act for a short period of time (for example, 60 seconds), rinses the tooth surface with water and dries it. Thereafter, one applies the formulation according to the invention in one or several layers with, for example, a small brush, dries it with an air flow and irradiates it with a commercially available polymerization lamp. Then the actual filling material is applied, for example, a polymerizable filling material standard in the dental field.

For purposes of a more detailed explanation, in the following are described: several examples (examples 1–7, 12 and 15) of the formulation according to the invention, the preparation of a formulation according to the invention in a preferred embodiment (example 7: simultaneous preparation of UDM and the formulation), the preparation of a polyester polyurethane-methacrylate (example 11) and a test of its effectiveness of the formulation by a) determining the shear bonding strength of dental fillings on dentin and, if applicable, enamel (examples 8, 13 and 16) and on dental alloys (example 10) and b) by determining the cavity adaptation (examples 9 and 14) subsequent to pretreatment with the formulation. (The silicon dioxide used in the examples has a mean particle size of 14 nm.)

Examples 1A and 5A are not according to the invention.

| Example 1 | A | B | C | D | E | F |
|---|---|---|---|---|---|---|
| Urethanedi-methacrylate (UDM 2) | 5.0 g | 4.0 g | 3.0 g | 2.5 g | 2.0 g | 1.0 g |
| 2-Hydroxy-ethylmeth-acrylate | — | 1.0 g | 2.0 g | 2.5 g | 3.0 g | 4.0 g |
| Acetone | 5.0 g | 5.0 g | 5.0 g | 5.0 g | 5.0 g | 5.0 g |
| Camphor quinone | 20 mg | 20 mg | 20 mg | 20 mg | 20 mg | 20 mg |
| Diallyl sulphonamide* | 50 mg | 50 mg | 50 mg | 50 mg | 50 mg | 50 mg |

Example 2A–E
The following formulations are produced by intensive mixing of the components.

| Example 2 | A | B | C | D | E |
|---|---|---|---|---|---|
| Urethanedimethacrylate (UDM 2) | 4.0 g | 3.0 g | 2.5 g | 2.0 g | 1.0 g |
| Glycerol monomethacrylate | 1.0 g | 2.0 g | 2.5 g | 3.0 g | 4.0 g |
| Acetone | 5.0 g | 5.0 g | 5.0 g | 5.0 g | 5.0 g |
| Camphor quinone | 20 mg | 20 mg | 20 mg | 20 mg | 20 mg |
| Diallyl sulphonamide* | 50 mg | 50 mg | 50 mg | 50 mg | 50 mg |

Example 3A–D
The following formulations are produced by intensive mixing of the components.

| Example 3 | A | B | C | D |
|---|---|---|---|---|
| Urethanedi(meth)acrylate | 2.5 g UDM 1 | 2.5 g UDA 4 | 2.5 g UDM 6 | 2.5 g UDM 7 |
| 2-Hydroxyethylmethacrylate | 2.5 g | 2.5 g | 2.5 g | 2.5 |
| Acetone | 5.0 g | 5.0 g | 5.0 g | 5.0 g |
| Camphor quinone | 20 mg | 20 mg | 20 mg | 20 mg |
| Diallyl sulphonamide* | 50 mg | 50 mg | 50 mg | 50 mg |

Example 4A–D
The following formulations are produced by intensive mixing of the components.

| Example 4 | A | B | C | D |
|---|---|---|---|---|
| Urethanedimethacrylate UDM 2 | 2.5 g | 2.5 g | 2.5 g | 2.5 g |
| 2-Hydroxyethylmethacrylate | 2.5 g | 2.5 g | 2.5 g | 2.5 g |
| Acetone | 5.0 g | 5.0 g | 5.0 g | 5.0 g |
| Silanized silicon dioxide** | 0.5 g | 1.0 g | 2.0 g | 3.0 g |
| Camphor quinone | 20 mg | 20 mg | 20 mg | 20 mg |
| Diallyl sulphonamide* | 50 mg | 50 mg | 50 mg | 50 mg |

Example 5A–F
The following formulations are produced by intensive mixing of the components.

| Example 5 | A | B | C | D | E | F |
|---|---|---|---|---|---|---|
| Urethanedi-methacrylate (UDM 2) | 5.0 g | 4.0 g | 3.0 g | 2.5 g | 2.0 g | 1.0 g |
| 2-Hydroxy-ethylmeth-acrylate | — | 1.0 g | 2.0 g | 2.5 g | 3.0 g | 4.0 g |
| Silanized silicon dioxide** | 1.0 g | 1.0 g | 1.0 g | 1.0 g | 1.0 g | 1.0 g |
| Acetone | 5.0 g | 5.0 g | 5.0 g | 5.0 g | 5.0 g | 5.0 g |
| Camphor quinone | 20 mg | 20 mg | 20 mg | 20 mg | 20 mg | 20 mg |
| Diallyl sulphonamide* | 50 mg | 50 mg | 50 mg | 50 mg | 50 mg | 50 mg |

Example 6A–D
The following formulations are produced by intensive mixing of the components.

| Example 6 | A | B | C | D |
|---|---|---|---|---|
| Urethanedimethacrylate UDM 2 | 3.0 g | 3.0 g | 3.0 g | 3.0 g |
| 2-Hydroxyethylmethacrylate | 2.0 g | 2.0 g | 2.0 g | 2.0 g |
| Acetone | 5.0 g | 5.0 g | 5.0 g | 5.0 g |
| 4-MET | 0.5 g | 1.0 g | 2.0 g | 3.0 g |
| Camphor quinone | 20 mg | 20 mg | 20 mg | 20 mg |
| Diallyl sulphonamide* | 50 mg | 50 mg | 50 mg | 50 mg |

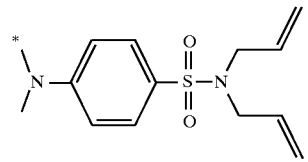

**Highly dispersed silica with a BET surface of 200 m²/g, and a mean particle size of 14 nm, silanized with γ-methacryloyloxypropyltrimethoxysilane

EXAMPLE 7

Simultaneous preparation of UDM 1 and a formulation according to the invention.

A mixture of 1 g hexamethylene diisocyanate, 4 g 2-hydroxy-ethylmethacrylate, 5 g acetone and 4 mg dibutyl tin-dilaurate (catalyst) is stirred for 10 hours at 40° C. After cooling, 1 g of 3-methacryloyloxypropyltrimethoxysilanesilanized silicon dioxide, 20 mg camphor quinone and 50 mg diallyl sulphonamide are added.

EXAMPLE 8

Determination of shear bonding strength to dentin

The effectiveness of the formulations described in examples 1–7 is tested by determining the shear bonding strength to dentin. Human teeth are being used which had been preserved in 1% chloramine solution for a maximum of three months after their extraction. Prior to their use in the bonding test and after a careful cleaning under running water, the teeth were stored in a physiological saline solution for a minimum of three and a maximum of ten days. On the day before their use in the bonding test, the teeth, lying on an approximal side, are individually embedded, with epoxy resin (Lekutherm® X20, curing agent T3), in cylindrical rubber molds having a diameter of 25 mm and a height of 12 mm. The teeth are ground by means of wet grinding with SiC papers with coarsenesses of 240, 320, 400 and 600 to the extent that a sufficiently large enamel-close dentin surface is exposed for bonding with a synthetic cylinder with a diameter of 3.5 mm. Subsequent to rinsing with de-ionized water and drying with an air flow, the conditioning agent Gluman® CPS gel (20% $H_3PO_4$, Bayer) is applied in a circular motion for 30 seconds using an absorbent cotton pellet, carefully rinsed with water and, by dabbing with cellucotton, superficially freed from surface water (wet technique). Three layers of the formulations from examples 1–7 are applied with a brush onto the conditioned dentin surface, dried with a compressed-air flow and irradiated with the TRANS-LUX® CL light device (Kulzer) for a duration of 20 seconds. The test samples pretreated in this manner are then clamped by means of a clamping device under double-part cylindrical teflon molds (diameter of 3.5 mm, height of 1 mm). Then the Teflon molds are filled with the resin based filling material PEKAFILL® (U, Bayer AG) by means of a syringe, covered with an $O_2$-impermeable strip and irradiated with the TRANSLUX® CL light device for 60 seconds. Immediately afterwards, the Teflon molds are removed and the cylindrical test samples stored in 37° C. warm water for a period of 24 hours until initiation of the shearing stress.

To determine the shear bonding strength, the cylindrical test samples which are provided with synthetic cylinders are stressed in a universal testing machine with the aid of a force piece parallel and close to the ground tooth surface, at a speed of 1 mm/minute, until the cylinder separates from the tooth. The shear bonding strength is the quotient of the breaking strength and the bonding surface (i.e. breaking strength per unit of area) and is determined on the basis of 5 test samples each. The results are indicated in Table I as their mean value.

Determination of shear bonding strength to enamel

For determination of the shear bonding strength to enamel treated with the formulations described in examples 1–7, extracted human teeth with intact labial enamel surfaces are embedded in epoxy resin and ground with wet SiC paper with a coarseness of 240 to 600, in order to expose a plane, peripheral enamel surface. The conditioning agent, Gluma® CPS gel, is applied onto the enamel surface and, after 30 seconds, is rinsed off carefully with de-ionized water. The drying is performed only superficially with a weak compressed-air flow, until the treated surface appears chalky white. All other steps are identical to the ones described above for determining the shear bonding strength to dentin. The values for the shear bonding strength to enamel are indicated in Table I.

TABLE I

| Formulation | Shear bonding strength to dentin | Shear bonding strength to enamel |
| --- | --- | --- |
| Example 1A | 8.2 MPa | 33.7 MPa |
| Example 1B | 17.7 MPa | 31.0 MPa |
| Example 1C | 17.2 MPa | 35.1 MPa |
| Example 1D | 17.2 MPa | 33.0 MPa |
| Example 1E | 18.3 MPa | 33.8 MPa |
| Example 1F | 16.5 MPa | 28.3 MPa |
| Example 2A | 11.3 MPa | not determined |
| Example 2B | 12.7 MPa | not determined |
| Example 2C | 14.7 MPa | not determined |
| Example 2D | 11.4 MPa | not determined |
| Example 2E | 13.2 MPa | not determined |
| Example 3A | 17.9 MPa | not determined |
| Example 3B | 19.7 MPa | not determined |
| Example 3C | 17.6 MPa | not determined |
| Example 3D | 17.5 MPa | not determined |
| Example 4A | 15.3 MPa | 33.4 MPa |
| Example 4B | 18.8 MPa | 34.8 MPa |
| Example 4C | 18.1 MPa | 26.6 MPa |
| Example 4D | 17.1 MPa | 31.1 MPa |
| Example 5A | 12.7 MPa | 29.6 MPa |
| Example 5B | 19.8 MPa | 32.1 MPa |
| Example 5C | 18.7 MPa | 33.5 MPa |
| Example 5D | 18.0 MPa | 32.4 MPa |
| Example 5E | 17.6 MPa | 35.4 MPa |
| Example 5F | 19.0 MPa | 29.7 MPa |
| Example 6A | 21.0 MPa | not determined |
| Example 6B | 25.0 MPa | not determined |
| Example 6C | 20.4 MPa | not determined |
| Example 6D | 16.5 MPa | not determined |
| Example 7 | 19.3 MPa | 32.3 MPa |

EXAMPLE 9

Cavity adaptation

An additional advantage can be seen with respect to the efficacy of a dental adhesive can be made based on examinations of the marginal gap of dental fillings which have been placed in dental cavities pretreated with the dental adhesive. In dentistry, intradental defects (cavities surrounded by the solid tooth substance) are generally filled with filling materials. Doing so creates wall-to-wall contraction stress, especially with polymerizable filling materials, due to the shrinking occurring during polymerization. Said stress is a contributing factor to the potential separation of the polymerizable filling from the cavity wall and thus the formation of marginal gaps in the area of the filling edge. The behavior of dental fillings with respect to cavity walls is called cavity adaptation. In principle, materials with high shear bonding strength do not necessarily result in good cavity adaptation, just as materials with poor shear bonding strength do not necessarily mean inferior cavity adaptation.

To examine the cavity adaptation, extracted, human molars were used, which had been preserved in 1% chloramine solution for a maximum of three months after their extraction. The teeth were surface-ground on one of their intact approximal sides with wet SiC papers with coarsenesses of 240, 320, 400 and 600 to the extent that sufficiently large enamel-proximate dentin surfaces were exposed.

Starting with the surface-ground dentin surfaces and into the dentin of the teeth, cylindrical cavities with a diameter of approx. 3 mm and a depth of approx. 1.5 mm were formed using water-cooling and fine-grained diamond preparation instruments on a manual dental implement operated with a micromotor. The edge angle of the cavities was 90°. The pretreatment of the cavities was with the Gluma® CPS gel conditioning agent for 30 seconds. Subsequently, the gel was carefully rinsed off with water and each cavity was superficially dried with a cotton pellet. Then, as in the bonding tests, two to three layers of the formulations described in the examples were applied onto the cavity walls with a brush. The thin layers remaining after removal of the solvent with compressed air were then irradiated for 20 seconds with light (TRANSLUX® CL) before the cavities were filled with the resin based filling material PEKAFILL® (U, Bayer AG), covered with a transparent strip and irradiated with light (TRANSLUX® CL) for a duration of 60 seconds. The teeth provided with fillings were then placed immediately into de-ionized water (23 C.°) for 15 minutes. Subsequently, any filling excesses were removed with wet SiC paper (coarsenesses 600 and 4000) until the edges of the cavities were exposed. Immediately thereafter an examination of the edge was performed under a reflected-light microscope (500-fold magnification). If marginal gaps did form between the fillings and the cavity walls, the maximum width of the marginal gaps was determined with the aid of a screw-type micrometer eyepiece. In Table II, the widths of the marginal gaps (mean values of 6 samples each) and the number of dental fillings without gaps between cavity wall and filling of 6 samples each are indicated.

TABLE II

| Formulation | Gap Width [μm] | Number of gap-free fillings |
|---|---|---|
| Example 1A | 4.1 | 0 |
| Example 1B | 1.4 | 1 |
| Example 1C | 0.7 | 3 |
| Example 1D | 0.7 | 2 |
| Example 1E | 1.2 | 1 |
| Example 1F | 2.3 | 0 |
| Example 5A | 4.2 | 0 |
| Example 5B | 1.8 | 0 |
| Example 5C | 0.2 | 5 |
| Example 5D | 0.3 | 5 |
| Example 5E | 0.1 | 5 |
| Example 5F | 0.8 | 1 |

EXAMPLE 10

Determination of shear bonding strength to the dental alloy Levochrom

In order to test the bonding strength of resin filling materials to dental alloys pretreated with the formulation according to the invention, the Levochrom (Bayer AG) CrCo casting alloy was used. Cube-shaped samples were cast from this alloy and, like the extracted teeth, embedded in epoxy resin. The samples were ground with SiC paper (coarsenesses of 240 to 600), blasted with 50 μm of special fused alumina, and cleaned for 5 minutes in deionized water in an ultrasonic bath. After drying the samples with compressed air, some of the formulations described in the examples were applied in two layers. Subsequently, after volatilization of the solvent, the samples pretreated in this manner were irradiated with the TRANSLUX® CL light device for a duration of 20 seconds and, corresponding to the bonding tests to dentin and enamel, connected with a cylinder (diameter of 3.5 mm, height of 1.5 mm) consisting of the resin filling material by means of photo-polymerization. The determination of the shear bonding strengths indicated in Table III was performed after 24-hour storage of the samples in 37° C. warm water, as described in example 8.

TABLE III

| Formulation | Shear bonding strength to Levochrom |
|---|---|
| Example 1C | 16.6 MPa |
| Example 6A | 19.4 MPa |
| Example 6B | 20.9 MPa |
| Example 6C | 20.8 MPa |
| Example 6D | 23.3 MPa |

EXAMPLE 11

Preparation of a polyester polyurethanemethacrylate (PEUDMA)

41.26 g of polyester DESMOPHEN HN 200 with a mean molecular weight of 2000 (aliphatic, OH-terminated polyester from adipic acid, neopentylglycol and hexanediol, manufacturer: Bayer AG), 0.06 g of 2,6 g-ditert-butylcresol, 0.06 g of dibutyl tin-dilaurate and 120 ml of absolute acetone are placed in a 250 ml triple-necked flask. At ambient temperature and while stirring, 4.2 g of hexamethylene diisocyanate are added dropwise. The reaction mixture is heated to 55° C. and stirred until the NCO content remains constant (approx. 20 hours). The checking of the NCO content is with IR-spectroscopy. After adding 1.3 g of 2-hydroxyethyl-methacrylate, stirring takes place for another 16 hours at 55° C. After this time period, NCO is no longer detectable. Sufficient acetone is added to form a 25% solution. The solution possesses good flowability and can be used directly for preparing the formulations according to the examples 12 and 15.

EXAMPLE 12

The following formulations are produced by intensive mixing of the components.

| Example 12 | A | B | C | D | E | F |
|---|---|---|---|---|---|---|
| Urethanedimethacrylate UDM 2 | 3.0 g | 3.0 g | 3.0 g | 3.0 g | 3.0 g | 3.0 g |
| 2-Hydroxy-ethylmethacrylate | 2.0 g | 2.0 g | 2.0 g | 2.0 g | 2.0 g | 2.0 g |
| PEUDMA (from example 11) | 0.0 g | 0.25 g | 0.5 g | 1.0 g | 2.0 g | 4.0 g |
| Acetone | 5.0 g | 5.0 g | 5.0 g | 5.0 g | 5.0 g | 5.0 g |
| Camphor quinone | 20 mg | 20 mg | 20 mg | 20 mg | 20 mg | 20 mg |
| Diallyl sulphonamide* | 50 mg | 50 mg | 50 mg | 50 mg | 50 mg | 50 mg |

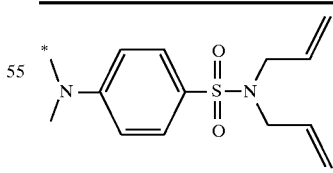

EXAMPLE 13

Determination of shear bonding strength to dentin

The formulations from example 12 are tested according to the procedure described in example 8. The shear bonding strength values are indicated in table IV.

TABLE IV

| Formulation | Shear bonding strength to dentin [MPa] |
|---|---|
| Example 12A | 15.4 ± 1.2 |
| Example 12B | 14.7 ± 1.1 |
| Example 12C | 14.9 ± 1.0 |
| Example 12D | 15.7 ± 1.4 |
| Example 12E | 15.0 ± 1.4 |
| Example 12F | 15.9 ± 2.9 |

EXAMPLE 14

Cavity adaptation

The formulations from example 12 are tested according to the procedure described in example 9. The values for gap width and number of gap-free fillings are indicated in Table V.

TABLE V

| Formulation | Gap Width [μm] | Number of gap-free fillings |
|---|---|---|
| Example 12A | 1.52 ± 1.31 | 2 |
| Example 12B | 0 | 6 |
| Example 12C | 0.48 ± 0.54 | 3 |
| Example 12D | 1.12 ± 1.09 | 2 |
| Example 12E | 1.13 ± 0.71 | 1 |
| Example 12F | 3.47 ± 1.41 | 0 |

EXAMPLE 15

The following formulations are produced by intensive mixing of the components.

| Example 15 | A | B | C | D | E | F |
|---|---|---|---|---|---|---|
| Urethanedi-methacrylate UDM 2 | 3.0 g | 3.0 g | 3.0 g | 3.0 g | 3.0 g | 3.0 g |
| 2-Hydroxy-ethylmeth-acrylate | 2.0 g | 2.0 g | 2.0 g | 2.0 g | 2.0 g | 2.0 g |
| PEUDMA (from example 11) | 0.0 g | 0.25 g | 0.5 g | 1.0 g | 2.0 g | 4.0 g |
| 4-META | 1.0 g | 1.0 g | 1.0 g | 1.0 g | 1.0 g | 1.0 g |
| Acetone | 5.0 g | 5.0 g | 5.0 g | 5.0 g | 5.0 g | 5.0 g |
| Camphor quinone | 20 mg | 20 mg | 20 mg | 20 mg | 20 mg | 20 mg |
| Diallyl sulphonamide* | 50 mg | 50 mg | 50 mg | 50 mg | 50 mg | 50 mg |

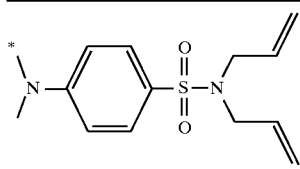

EXAMPLE 16

Determination of shear bonding strength to dentin

The formulations from example 15 are tested according to the procedure described in example 8. The shear bonding strength values are indicated in Table VI.

TABLE VI

| Formulation | Shear bonding strength to dentin [MPa] |
|---|---|
| Example 15A | 17.5 ± 1.8 |
| Example 15B | 19.5 ± 4.7 |
| Example 15C | 19.0 ± 3.5 |
| Example 15D | 18.7 ± 1.2 |
| Example 15E | 16.0 ± 2.5 |
| Example 15F | 16.0 ± 3.6 |

It will be appreciated that the instant specification is set forth by way of illustration and not limitation, and that various modifications and changes may be made without departing from the spirit and scope of the present invention.

What is claimed is:

1. A formulation for use as an adhesive component, said formulation consisting of a) 10–40% by weight of an hydroxyalkyl(meth)acrylate, b) 10–40% by weight of an urethanedi(meth)acrylate, selected from the urethanedi(meth)acrylates according to formulas I to VII

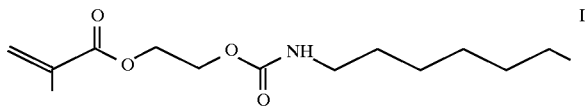 I

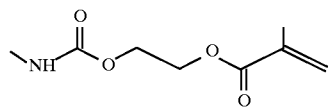

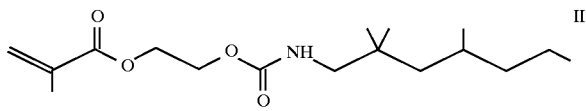 II

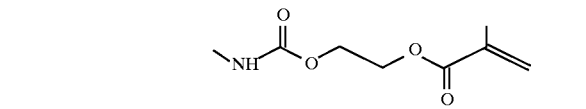

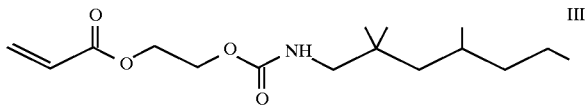 III

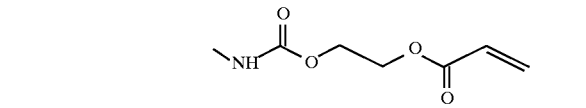

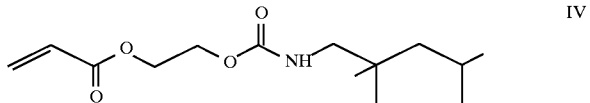 IV

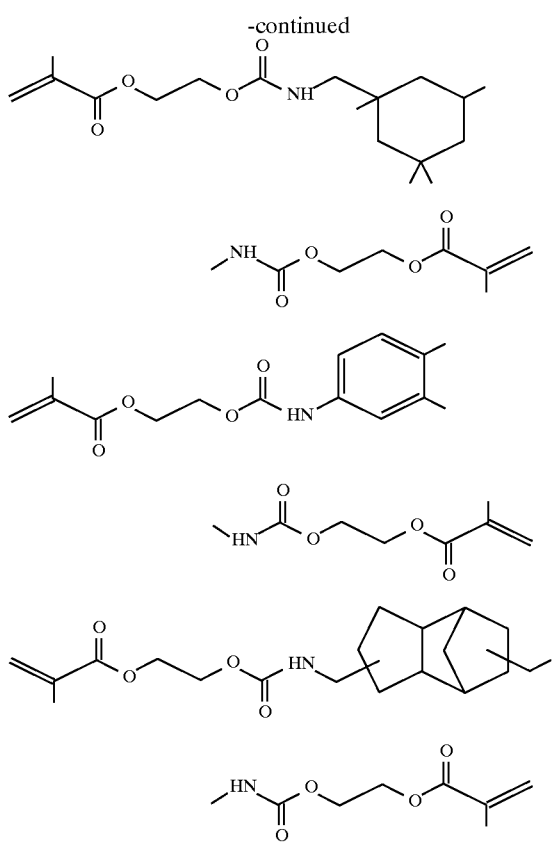

c) 30–70% by weight of a volatile solvent miscible with water, d) 0.01–2.5% by weight of a photo-initiator and e) 0–40% by weight of generally known additives.

2. A formulation according to claim 1, wherein said additives e) comprise e1) 5–20% by weight of a filler.

3. A formulation according to claim 2, wherein said filler is highly dispersed silica with a mean particle size of 5–2000 nm.

4. A formulation according to claim 3 wherein the mean particle size of the highly dispersed silica is 10–100 nm.

5. A formulation according to claim 1 containing at least 5% of said additives e).

6. A formulation according to claim 1, wherein said additives e) comprise e3) 1–30% by weight of polyether (meth)acrylates, polyester (meth)acrylates or polyester polyurethane(meth)acrylates.

7. A formulation according to claim 6, wherein said polyether (meth)acrylates are polyethylene glycoldi(meth)acrylates.

8. A formulation according to claim 1, wherein said additives e) comprise e2) 5–30% by weight of esters of aromatic tri- or tetra-carboxylic acids possessing methacryloyloxy groups or of the corresponding anhydrides.

9. A formulation according to claim 8, wherein the additives e) comprise e2) 5–30% by weight of 4-MET or 4-META.

10. In a method of applying a polymerizable dental restoration material to a tooth, the improvement wherein the formulation according to claim 1 is used as an adhesive component treatment of the hard substance of the tooth.

11. In a method of performing dental restoration of applying a polymerizable dental restoration material to a tooth, the steps of (a) mechanically cleaning the tooth surface;

(b) applying a conditioning fluid comprising an acid and having a pH of 0.1 to 3.5, to the tooth surface;

(c) rinsing the tooth surface with water and drying the tooth surface;

(d) thereafter applying at least one layer of the bonding agent formulation according to claim 1;

(e) drying the applied formulation with an air flow and then irradiating the dried formulation to polymerize it; and thereafter, (f) applying the dental restoration material to the tooth.

12. A method for preparing the formulation according to claim 1, comprising the steps of reacting a diisocyanate with a surplus of hydroxyalkyl (meth)acrylate in a volatile solvent miscible with water in the presence of a catalyst to form urethanedi(meth)acrylate; and thereafter adding and reacting the additional components as defined in claim 1.

* * * * *